United States Patent [19]
Sundman

[11] Patent Number: 5,941,835
[45] Date of Patent: Aug. 24, 1999

[54] SYSTEM AND METHOD FOR DETERMINING PRESSURE DISTRIBUTION ACROSS THE SOLE OF A FOOT

[75] Inventor: Arjen Sundman, Santa Cruz, Calif.

[73] Assignee: Amfit, Inc., Santa Clara, Calif.

[21] Appl. No.: 08/905,649

[22] Filed: Aug. 4, 1997

[51] Int. Cl.$^6$ ........................................................ A61B 5/00
[52] U.S. Cl. ............................................ 600/592; 73/172
[58] Field of Search .............................. 73/172; 600/592, 600/587, 595; 12/142 N, 146 M

[56] References Cited

U.S. PATENT DOCUMENTS

| | | | |
|---|---|---|---|
| 2,378,039 | 6/1945 | Schenker | 73/172 |
| 4,517,696 | 5/1985 | Schartz | 12/1 R |
| 4,876,758 | 10/1989 | Rolloff et al. | 12/142 |

Primary Examiner—Richard Chilcot
Assistant Examiner—Willie Morris Worth
Attorney, Agent, or Firm—Ohlandt, Greeley, Ruggiero & Perle

[57] ABSTRACT

The method of the invention maps pressure applied by resilient body surface onto a plurality of movable gauge pins. The method includes the steps of: providing relative movement between the resilient body and the movable gauge pins to cause the gauge pins to come into contact with the body so as to define a three dimensional surface which approximates the surface of the body; measuring the position of each of the gauge pins as a reference position of each; using a spring element to apply a pressure to each of the gauge pins; measuring a position of each of the gauge pins after application of the pressure, to determine a test position of each gauge pin; subtracting the reference position of each gauge pin from the test position of each gauge pin to determine a pressure displacement of each gauge pin; and utilizing the pressure displacement and a spring constant of the spring elements which applied the pressure to the movable gauge pins to derive a pressure exerted upon each gauge pin by the resilient body surface to enable a subsequent analysis thereof.

12 Claims, 5 Drawing Sheets

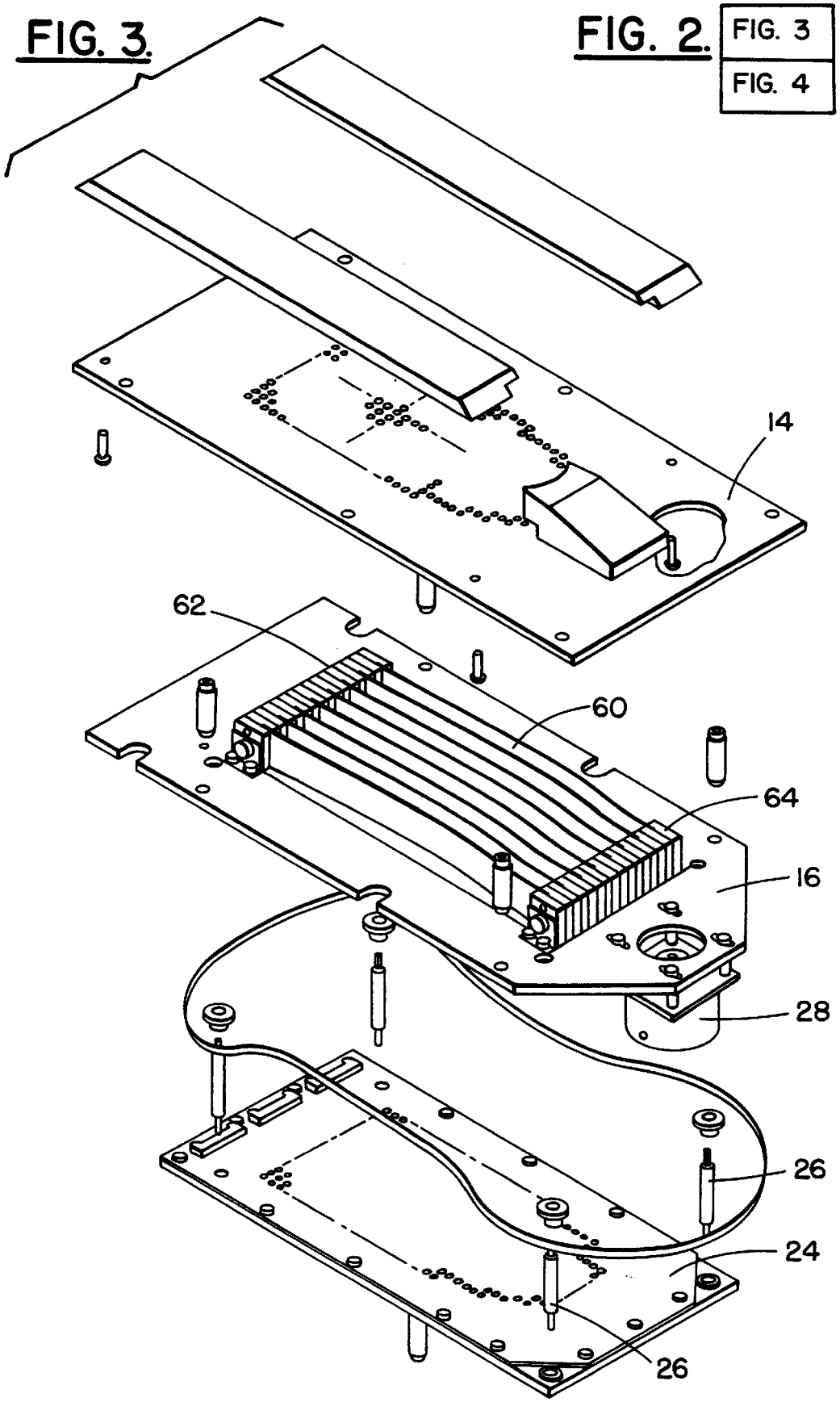

SYSTEM AND METHOD FOR DETERMINING PRESSURE DISTRIBUTION ACROSS THE SOLE OF A FOOT

FIELD OF THE INVENTION

This invention relates to a method and apparatus for determination of pressure points under the plantar aspect of a patient's foot and, more particularly, to an apparatus and method for enabling the mapping of pressure distribution across the plantar aspect of a foot.

BACKGROUND OF THE INVENTION

Foot pain can result from a number of causes, including neuroma, poorly designed, ill-fitting footwear, fatigue and pressure points. A number of diagnostic techniques are now used to determine pressure points and to assess pressure distribution across the sole of a foot. One system employs an array of scales or load cells under the foot to map the foot pressure as weight is placed thereupon. Such arrays are called force plate arrays and evidence both accurate and repeatable measurements of pressure values. The disadvantage of such arrays is that the individual scales/load cells are expensive, thereby limiting the number thereof and at best, providing a limited number of pressure samples across the sole of a foot.

A second pressure diagnostic system utilizes a membrane array that is similar to arrays developed for computer keyboards. The membrane array includes three polymer layers, with a top layer provided with conductors running in columns and a bottom layer provided with conductors running in rows. An intermediate insulator layer is provided with holes at each intersection of the column/row conductors. In general, the conductors are comprised of conductive inks which do not exhibit high levels of conductivity. Thus, when the conductive layers are pressed together by foot pressure, there is initially a high level of contact resistance which, if the foot pressure is increased, decreases. The reduction in resistance is indicative of the applied pressure.

Such membrane arrays can be inserted into shoes to obtain pressure data during walking or running. They also provide a high data density and are relatively inexpensive. However, their changes in resistance in response to pressure are quite variable and an array generally must be replaced after a few scans, as the inks are abraded during each use (causing a further change in the resistance values). Finally, each membrane array must be recalibrated before use—as a result of changes in the conductor condition during previous uses.

There is a need for a system and method which will provide a highly dense set of measurements of pressure values from the plantar aspect of a foot. Further, it is important that the measurement mechanism provide both repeatable and accurate pressure results to enable reliable diagnosis of foot problems.

U.S. Pat. No. 4,876,758 to Rolloff et al., assigned to the same Assignee as this Application, illustrates a foot impression unit which is provided with an array of gauge pins that are vertically movable into engagement with the sole of a patient's foot. A control mechanism urges the gauge pins into contact with the foot to form an impression of the under-surface thereof. A locking mechanism releasably locks the gauge pins in place to retain that impression and a magnetic/Hall effect sensing mechanism scans the gauge pins to produce signals indicative of the positions thereof. The mechanism for moving the gauge pins into engagement with the foot is a diaphragm which can be pneumatically expanded to cause the gauge pins to rise within their guide holes until they contact the sole of the foot. As will become apparent from the description below, substantial portions of the unit described in the Rolloff et al. patent are incorporated in the invention hereof and the description and disclosure of the Rolloff et al patent '758 are therefore incorporated herein by reference.

It is an object of this invention to provide a system and method for enabling an accurate pressure measurement map to be produced of the plantar aspect of a foot.

It is another object of this invention to provide a system and method for mapping pressure points on the sole of a foot and enabling a highly dense and repeatable set of pressure measurements to be obtained.

SUMMARY OF THE INVENTION

The method of the invention maps pressure applied by resilient body surface onto a plurality of movable gauge pins. The method includes the steps of: providing relative movement between the resilient body and the movable gauge pins to cause the gauge pins to come into contact with the body so as to define a three dimensional surface which approximates the contacting surface of the body; measuring the position of each of the gauge pins as a reference position of each; using a spring element to thereafter apply a pressure to each of the gauge pins; measuring a position of each of the gauge pins after application of the pressure, to determine a test position of each gauge pin; subtracting the reference position of each gauge pin from the test position of each gauge pin to determine a pressure displacement of each gauge pin; and utilizing the pressure displacement and a spring constant of the spring elements which applied the pressure to the movable gauge pins to derive a pressure exerted upon each gauge pin by the resilient body surface to enable a subsequent analysis thereof.

BRIEF DESCRIPTION OF THE DRAWINGS

FIG. 2 illustrates the arrangement of FIGS. 3 and 4.

FIG. 3 is an exploded view of the uppermost portions of the pressure measurement apparatus of FIG. 1.

DETAILED DESCRIPTION OF THE INVENTION

Figure 1:
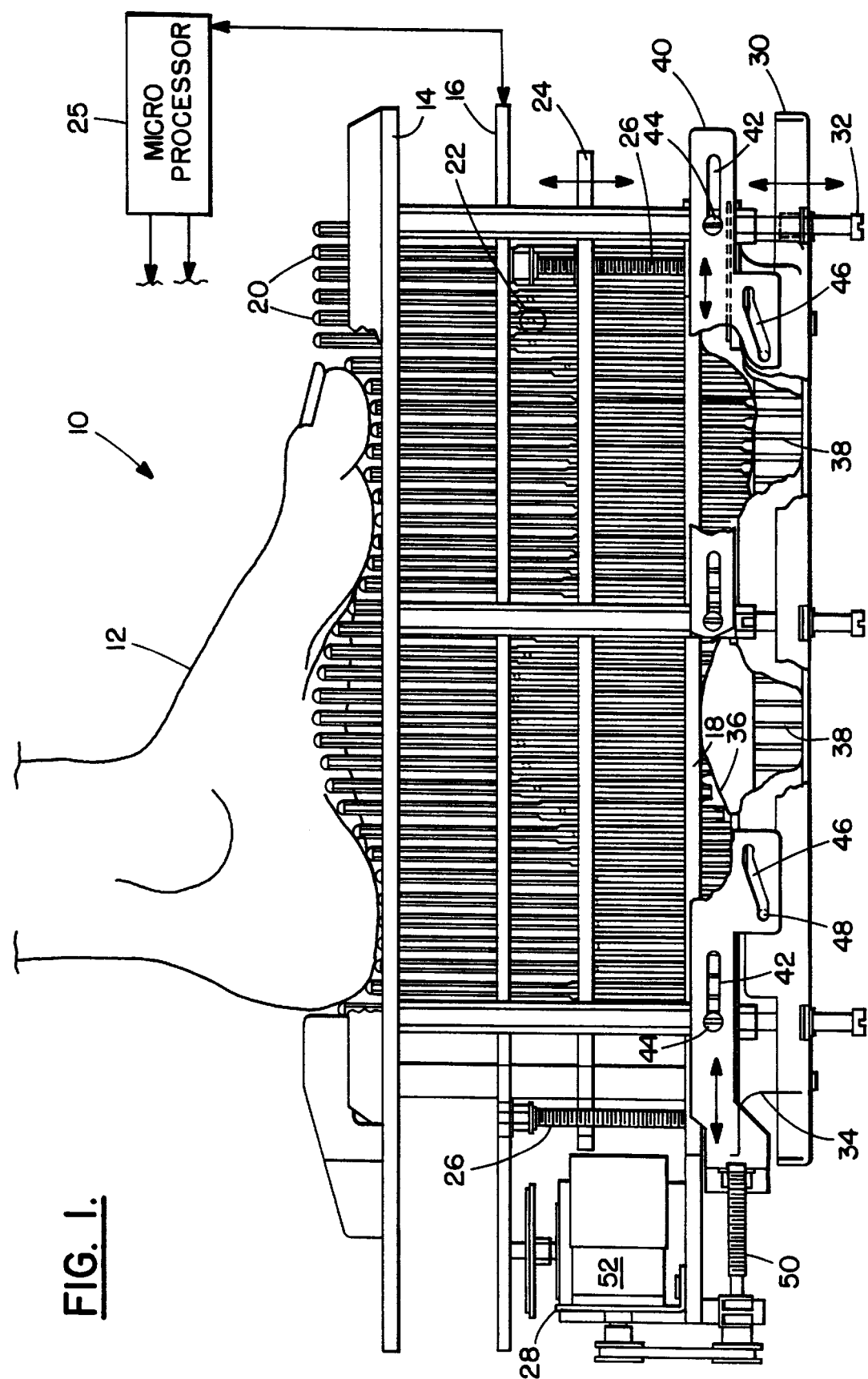
FIG. 1 is a schematic side view of a pressure measurement apparatus for performing the invention.
Figure 4:
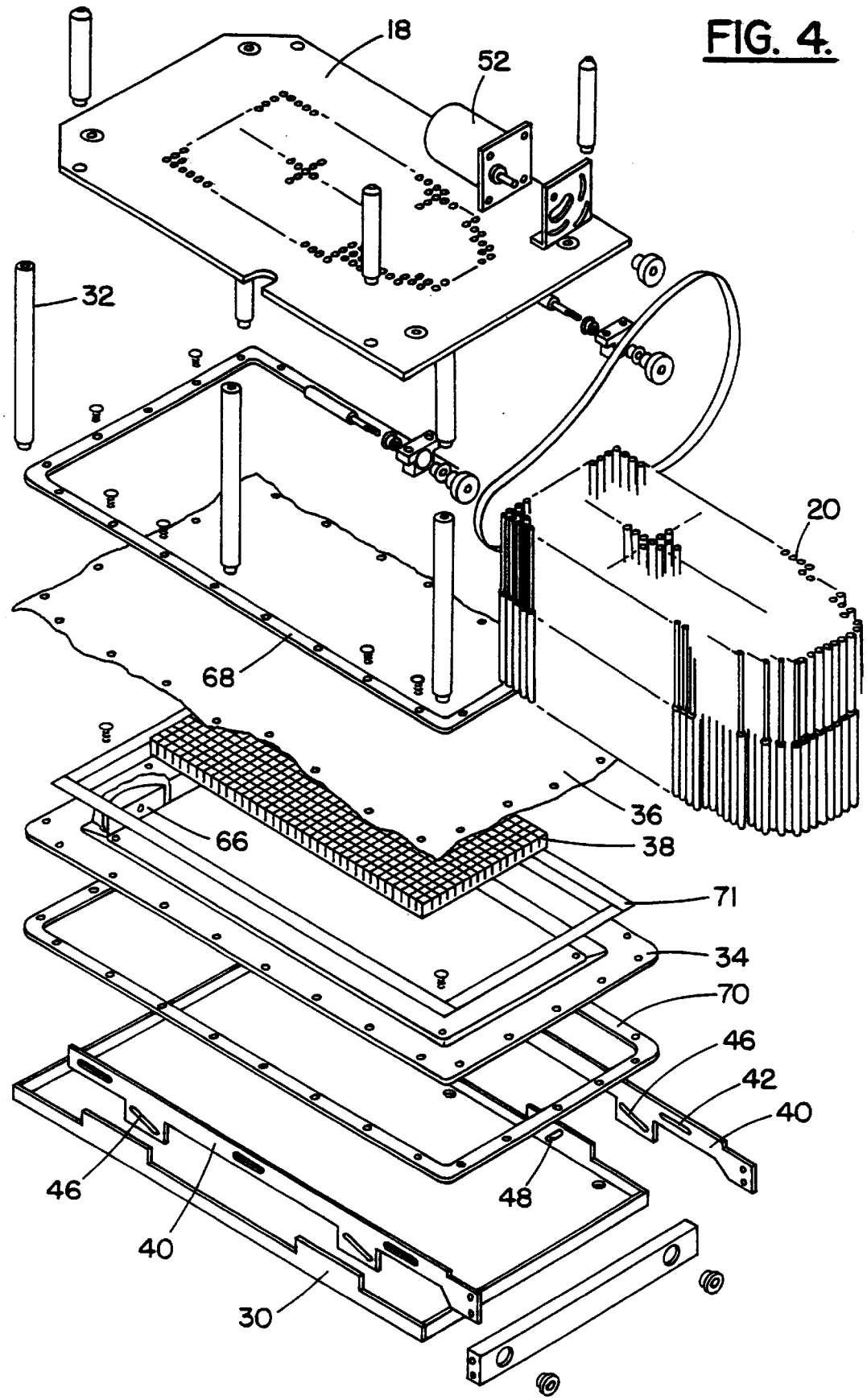
FIG. 4 is an exploded view of the lowermost portions of the pressure measurement apparatus of FIG. 1.

As will be hereafter understood, the structure of pressure measurement apparatus 10 bears substantial resemblance to the system for forming custom-made shoe inserts described in U.S. Pat. No. 4,876,758. However, certain modifications have been made to that structure to adapt it to the mapping of pressure points on the sole of a foot 12. FIG. 1 illustrates a side schematic view of pressure measurement apparatus 10, whereas FIGS. 3 and 4 show an exploded view thereof. Like components are numbered identically in all views. FIG. 2 illustrates the top/bottom organization of FIGS. 3 and 4.

Turning to FIG. 1, pressure measurement apparatus 10 includes three plates, i.e., a foot support plate 14, an upper guide plate 16 and a lower guide plate 18. Each of plates 14, 16 and 18 is provided with an array of aligned holes which slidably receive gauge pins 20. Each gauge pin 20 is provided with a magnet structure 22 which is used to enable determination of the position of the respective gauge pin.

A circuit board 24 is mounted on a plurality of lead screws 26 and is vertically movable as lead screws 26 are rotated by a drive belt which is, in turn, coupled to scan motor 28. Circuit board 24 includes a Hall sensor positioned adjacent each gauge element 20. A microprocessor 25 is coupled to each of the Hall sensors and to the various motors which operate portions of pressure measurement apparatus 10.

In order to determine the position of each gauge pin 20, motor 28 causes circuit board 24 to travel, for example, to its lowermost position. Then, circuit board 24 is moved upwardly by lead screws 26, enabling each Hall sensor to sense the position of a magnet structure in each gauge pin 20. In such manner, the position of each gauge pin is detected, based upon the distance of travel of circuit board 24 and the point at which a respective magnet structure induces its associated Hall sensor to provide an output to microprocessor 25. The outputs from each Hall sensor are then processed to determine the gauge pin positions in a manner to be described below.

A base plate 30 is slidably mounted on a plurality of posts 32. Base plate 30 supports an air container 34 which is sealed by a diaphragm 36. An air supply (not shown) is coupled to air container 34 and is adapted to pressurize air container 34 so as to cause an inflation and upward movement of diaphragm 36. The upward movement of diaphragm 36 pushes gauge pins 20 in an upward direction until they engage the sole of foot 12.

Positioned within air container 34 is an array of springs elements 38, each of which manifests a substantially identical spring rate. Each spring element 38 is positioned to engage a corresponding gauge pin 20. The array of spring elements 38 may be comprised of individual springs or, more preferably, comprised of a resilient polymeric material evidencing a known resilience characteristic. Such materials include cellular urethane.

A pair of slider plates 40 (only one is shown in FIG. 1) include horizontal travel slots 42 which slide on pins 44 to enable horizontal reciprocating movement of the respective slider plates 40. A pair of cam slots 46 in each slider plate 40 engage pins 48 that extend from base plate 30.

The leftmost end of each slider plate 40 is engaged by a lead screw 50 which is, in turn, driven by a motor 52. Rotation of motor 52 results in lead screws 50 causing a left-to-right or right-to-left movement of slider plates 40. Through the interaction of pins 48 and cam slots 46, a leftward movement of slider plates 40 causes an upward displacement of base plate 30 and spring elements 38. A reverse direction movement of slider plates 40 causes a downward traversal of base plate 30 and a disengagement of spring elements 38 from gauge pins 20.

Referring briefly to FIGS. 3 and 4, an exploded view of the principal components of pressure measurement apparatus 10 are shown. Omitted from FIG. 1, but shown in FIG. 3 are a plurality of elongated inflatable tubes 60 that are mounted on guide plate 16. Each of inflatable tubes 60 is of a generally rectangular cross section and spans between retainers 62 and 64. Upon inflation thereof, tubes 60 expand and grip gauge pins 20 which pass therebetween. Such action acts to clamp gauge pins 20 in position.

As shown in FIG. 4, air container 34 includes a pneumatic input 66 which enables the inflation or deflation of diaphragm 36. A pair of clamps 68 and 70 and a gasket 71 seal diaphragm 36 to air container 34. As can further be seen in FIG. 4, gauge pins 20 comprise an array of pins, with each gauge pin enabling an individual position measurement to be taken of the sole of foot 12.

Figure 5:
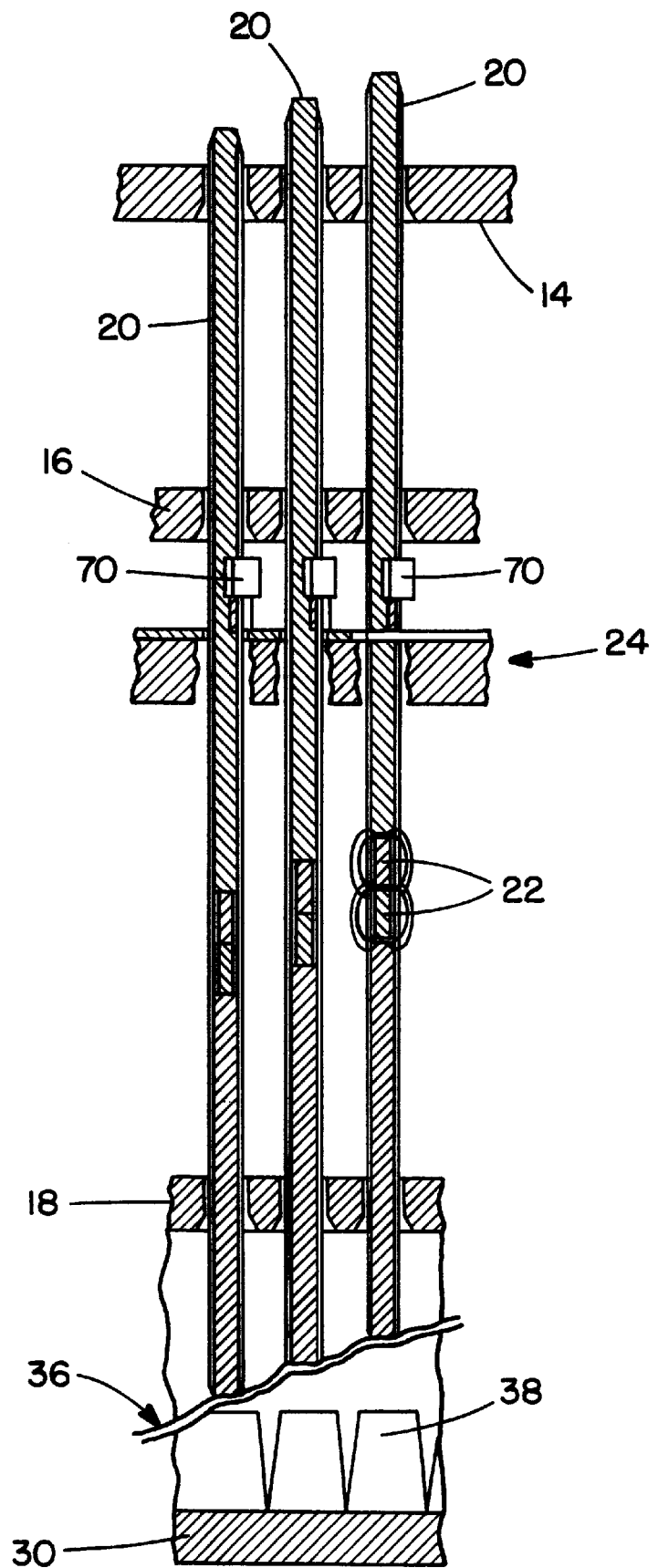
FIG. 5 illustrates plural gauge pins with magnets embedded therein and their respective relationships to Hall-effect sensors that are positioned to determine the amount of extension of each gauge pin.

Turning briefly to FIG. 5, further detail is shown of the arrangement of gauge pins 20, magnetic structures 22 and Hall sensors 70 that are mounted on circuit board 24. Gauge pins 20 are initially positioned against the underside of foot 12. At such time, circuit board 24 is moved to support plate 18 and is then raised upwardly, causing Hall sensors 70 to pass magnetic structures 22 and to have induced therein signals by magnetic structures 22. By determining the time of occurrence of the signal outputs from Hall sensors 70, and knowing the position of circuit board 24, the position of each of magnetic structures 22 can be determined by microprocessor 25, with high accuracy.

Returning to FIG. 1 (in conjunction with FIGS. 3–5), the operation of the invention will be described. Initially, foot 12 is placed upon support plate 14 and air is introduced into air container 34 to cause an inflation of diaphragm 36. The inflation of diaphragm 36 causes an upward movement of gauge pins 20 until they contact the sole of foot 12. At such time, gauge pins 20 are clamped in place by action of inflatable tubes 60 (FIG. 3). Circuit board 24 is positioned against lower plate 18 and is then moved upwardly. This scanning action enables the position of each of magnet structures 22 to be determined and, thus, the position of each of gauge pins 20. Hereafter, this initial position will be referred to as the "reference" position of each gauge pin 20.

During the aforesaid operation of pressure measurement apparatus 10, slider plate 40 is maintained in its rightmost position, thereby positioning base plate 30 in its lowermost orientation, with spring elements 38 out of contact with gauge pins 20. To now perform a pressure measurement, gauge pins 20 are unclamped and motor 52 is operated by microprocessor 25 to cause a leftward movement of slider plate 40. Such action causes an upward camming of pins 48 by slots 46 and results in an upward movement of base plate 30. Such upward movement causes the upper surfaces of spring elements 38 to engage a lowermost subset of gauge pins 20.

As each of spring elements 38 moves upwardly, certain ones thereof engage the lowermost-positioned gauge pins 20 and exert an upward force thereon. The cumulative effect of this upward force is sufficient to preferably lift foot 12 up, even though a person is standing with full weight bearing on the foot. The spring force exerted, via gauge pins 20, on the sole of foot 12 deflects soft areas of the sole and is resisted by harder areas. Accordingly, certain ones of spring elements 38 are compressed more than others as a result of the softness/hardness of the sole of foot 12.

If foot 12 were not positioned as shown in FIG. 1, all of gauge pins 20 would move upwardly by a common amount as a result of the like spring rates of spring elements 38. However, the pressure exerted by portions of foot 12 on the contacting gauge pins prevents the upward movement of the respective gauge pins and thereby causes a compression of respectively coupled spring elements 38.

Once slider plate 40 has been moved its full extent to the left and gauge pins 20 have been extended (or not) and clamped into position, circuit board 24 is again scanned over gauge pins 20 to determine the resulting positions thereof. The resulting positions of gauge pins 20 will hereafter be referred to as the "test" positions. Accordingly, at this point, microprocessor 25 now has an array of values which indicates the reference positions of each of gauge pins 20 and an array of position values which indicate the test positions of each of gauge pins 20.

Initially, microprocessor 25 subtracts the reference position from the test position of each gauge pin 20 so as to normalize each of the gauge pin positions. This calculation yields the amount each gauge pin 20 was deflected, less the variable effect of the contour of the underside of foot 12.

Given the initial height of each of spring elements 38, the length of each of gauge pins 20 and the normalized position of each gauge pin 20, the amount of compression of each spring element 38 can be calculated. Given, further, a knowledge of the spring rate of each spring element 38, the amount of pressure required to depress each of spring elements 38 by the measured amount can then be calculated, to enable an array of pressure values to be determined, one for each gauge element 20.

Figure 6:
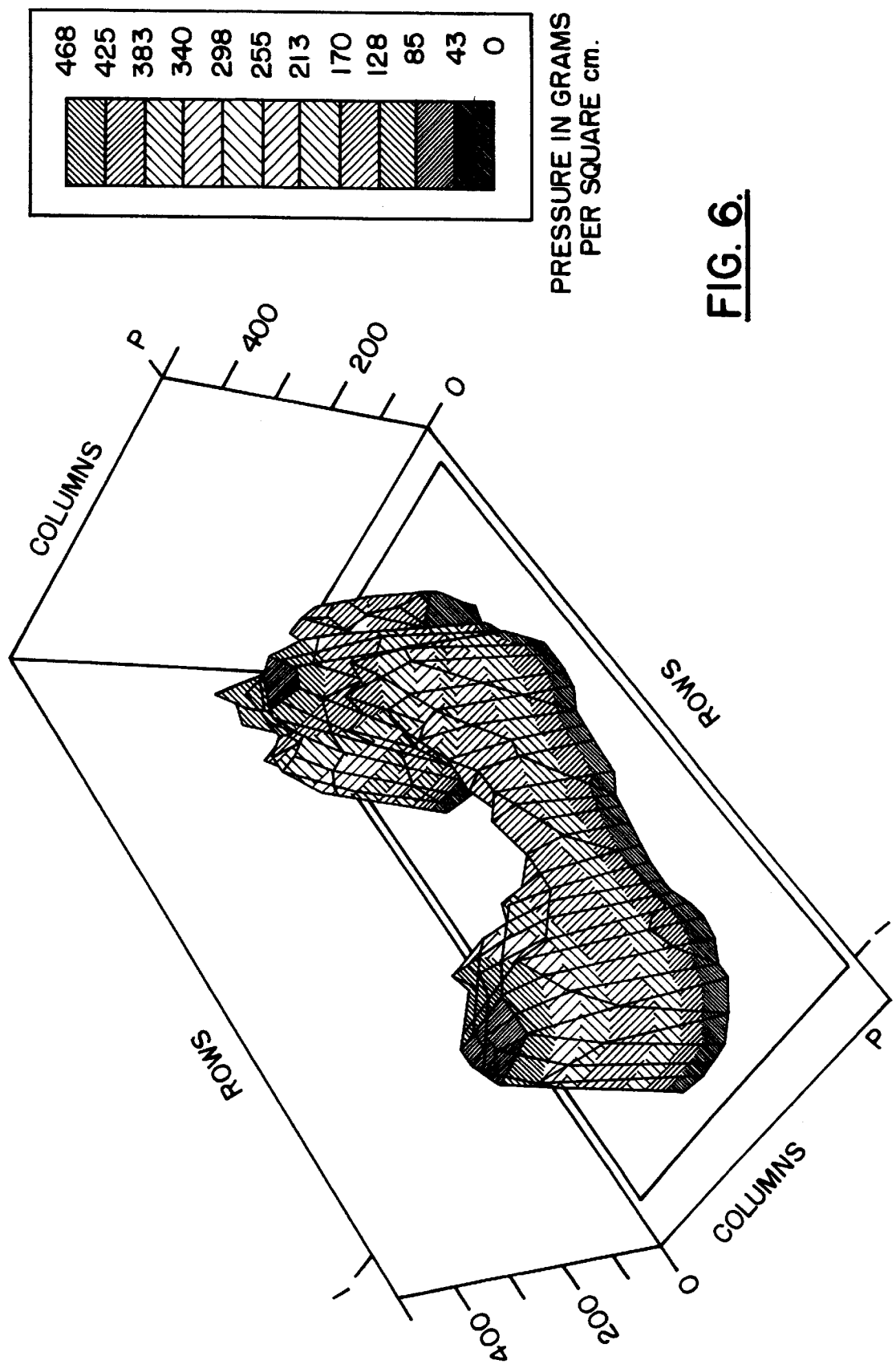
FIG. 6 is a 3-dimensional pressure graph that is derived by analysis of the pressure readings from the pressure measurement apparatus of FIG. 1.

Thereafter, a 3-dimensional pressure plot may be generated such as is shown in FIG. 6. Examination of such a pressure plot, given an abnormal position of pressure peaks, will indicate to the physician the precise position of abnormal pressure distributions on the sole of a patient's foot. Further, by comparing the pressure map shown in FIG. 6 with a compiled data base of normal pressure maps, regions of abnormality can be detected and highlighted for viewing by the physician.

To determine the spring rates of spring elements 38, the following procedure may be utilized. A single spring element is placed on a scale and the scale is zeroed to compensate for the weight of the spring element, itself. A force is applied against the top of the spring element until the spring element is depressed approximately 10% of the distance that base plate 30 will be moved by slider plate 40. In a test system, this distance was approximately 0.6 mm. The weight on the scale is then noted and the procedure is repeated for 20%, 30% . . . to 100% of the travel distance of base plate 30 (e.g. 6.0 mm). Thereafter, weight, as determined from the scale, is plotted versus deflection of the spring element. Certain polymeric foam materials exhibit an almost linear relationship of weight versus deflection. A preferred material is cellular urethane.

Assuming a linear relationship between weight versus deflection, the spring rate of a spring element that deflects 0.6 mm with 100 grams of weight applied is 167 grams per millimeter (100/0.6).

Using the thus-derived spring rate, pressure can be determined over the sole of the foot. If the gauge pins are 8 mm on center and the spring rate is 167 grams per millimeter, then the following calculation will yield grams per square centimeter. Assuming that there are 1.56 gauge pins per square centimeter (with each gauge pin covering an area of 64 sq. millimeters), the spring rate multiplied by the square cm area per gauge pin yields pressure per square cm. Thus, given a spring rate of 167 grams per millimeter, 167×1.56= 260 grams/sq. cm/mm of deflection.

To determine the pressure measured by any gauge pin 20, the gauge pin deflection, after the above indicated normalization, is accessed and is multiplied by the value of force per sq. centimeter per millimeter of deflection derived as indicated above.

It should be understood that the foregoing description is only illustrative of the invention. Various alternatives and modifications can be devised by those skilled in the art without departing from the invention. For instance, while spring elements 38 are preferably formed from a block of cellular urethane, they could be configured as individual springs that would be able to urge gauge elements 20 upward without the air inflated diaphragm. Such a design would not be limited by the elasticity of diaphragm 36, but would be more expensive than the preferred embodiment of the invention. Accordingly, the present invention is intended to embrace all such alternatives, modifications and variances which fall within the scope of the appended claims.

I claim:

1. A method for determining a weight applied by a resilient body surface, said method employing a plurality of movable gauge pins and comprising the steps of:

a) enabling relative movement between said resilient body surface and said gauge pins to bring tips of said gauge pins into contact with said body surface so as to cause said tips to define a reference body surface;

b) measuring a position of each said gauge pin to define a reference position therefor;

c) applying a pressure, via a spring means, to at least a subset of said gauge pins, and via said subset of gauge pins, to said resilient body surface;

d) measuring a position of each gauge pin of said subset of gauge pins as a test position of each said gauge pin;

e) deriving a difference between said test position and said reference position for each one of said subset of gauge pins, each said difference being a displacement due to application of said pressure; and f) employing each said displacement and a characteristic of said spring means to determine a weight applied by said resilient body surface to each gauge pin of said subset of gauge pins.

2. The method as recited in claim 1, wherein said characteristic of said spring means is a spring rate having dimensions of displacement units of said spring means per applied weight unit.

3. The method as recited in claim 1, comprising the added step of:

g) displaying weight data determined in step f), correlated to individual gauge pins, so as to represent a distribution of weight across said subset of gauge pins.

4. The method as recited in claim 1, wherein said resilient body surface is the plantar aspect of a foot.

5. A system for determining a weight applied by a resilient body surface, said system comprising:

a plurality of movable gauge pins;

means for moving said gauge pins into contact with said resilient body surface so as to cause tips of said gauge pins to define a reference body surface;

spring means for applying pressure to at least a subset of said gauge pins, and via said tips of said subset of gauge pins, to said resilient body surface;

sense means, operative after operation of said means for moving, for measuring a position of each said gauge pin to define a reference position therefor and further operative, after operation of said spring means, for measuring a position of each said gauge pin to define a test position therefor; and processor means for deriving a difference between said test position and said reference position for each one of said subset of gauge pins, each said difference being a displacement due to application of said pressure, and for employing each said displacement and a characteristic of said spring means to determine a weight applied by said resilient body surface to each gauge pin of said subset of gauge pins.

6. The system as recited in claim 5, wherein said characteristic of said spring means is a spring constant having dimensions of displacement units of said spring means per applied weight unit.

7. The system as recited in claim 5, wherein said processor means displays weight data, correlated to individual gauge pins, so as to represent a distribution of weight across said subset of gauge pins.

8. The system as recited in claim 5, wherein said resilient body surface is the plantar aspect of a foot.

9. The system as recited in claim 5, wherein said spring means comprises a plurality of polymeric, resilient spring elements, one spring element for each gauge pin.

10. The system as recited in claim 9, wherein said plurality of polymeric, resilient spring elements are formed from a block of cellular urethane.

11. The system as recited in claim 9, wherein each of said plurality of polymeric, resilient spring elements is formed of cellular urethane.

12. The system as recited in claim 9, wherein said spring means further includes a platform for supporting said plurality of polymeric, resilient spring elements and for moving said spring elements into and out of engagement with said gauge pins.

* * * * *